United States Patent [19]

Murata

[11] Patent Number: 5,639,645
[45] Date of Patent: Jun. 17, 1997

[54] RECOMBINANT Δ9 DESATURASE AND A GENE ENCODING THE SAME

[75] Inventor: Norio Murata, Okazaki, Japan

[73] Assignees: Mitsubishi Corporation; Mitsubishi Chemical Corporation, both of Tokyo; Tohoku Electric Power Company, Incorporated, Miyagi, all of Japan

[21] Appl. No.: 309,182

[22] Filed: Sep. 20, 1994

[30] Foreign Application Priority Data

Sep. 22, 1993 [JP] Japan ................... 5-236720

[51] Int. Cl.$^6$ .............. C12N 9/02; C12N 1/21; C12N 15/63; C07H 21/04
[52] U.S. Cl. ............ 435/189; 435/252.3; 435/320.1; 536/23.2
[58] Field of Search ............. 536/23.2; 435/320.1, 435/252.3, 189

[56] References Cited

U.S. PATENT DOCUMENTS 5,552,306  9/1996  Thomas et al. ................... 435/134

FOREIGN PATENT DOCUMENTS 0 550 162 A1  7/1993  European Pat. Off.
WO91/13972  9/1991  WIPO.

OTHER PUBLICATIONS

Higashi, S. et al. (1993) "An in vivo study of substrate specificities of acyl–lipid desaturases and acyltransferases in lipid synthesis in Synechocystis PCC6803" Plant Physiol. 102(4):1275–1278. Aug. 1993.

Wada et al. Nature vol. 347 13 Sep. 1990, pp. 200–203.

Reddy et al. Plant Molecular Biology 27: pp. 293–300, 1993.

Sakamoto et al. Plant Molecular Biology 24: pp. 643–650, 1994.

H. Wada et al., "Temperature–Induced Changes in the Fatty Acid Composition of the Cyanobacterium, Synechocystis PCC6803[1]", Plant Physiol. vol. 92, pp. 1062–1069, 1990.

H. Wada et al., "Enhancement of Chilling Tolerance of a Cyanobacterium by Genetic Manipulation of Fatty Acid Desaturation", Letters to Nature, vol. 347, pp. 200–203, Sep. 13, 1990.

T. Sakamoto et al., "Δ9 Acyl–Lipid Desaturases of Cyanobacteria", The Journal of Biological Chemistry, vol. 269, No. 41, pp. 25576–25580, Oct. 14, 1994.

*Primary Examiner*—Robert A. Wax
*Assistant Examiner*—Kawai Lau
*Attorney, Agent, or Firm*—Wenderoth, Lind & Ponack

[57] ABSTRACT

An isolated gene encoding Δ9 desaturase of cyanobacteria, an expression vector containing the same, a transformant transformed therewith and a recombinant Δ9 desaturase are provided, wherein said gene is useful for improving the composition of fatty acids of animals, plants and microorganisms by transformation and for producing animals, plants or microorganisms which tolerate low temperature.

5 Claims, No Drawings

RECOMBINANT Δ9 DESATURASE AND A GENE ENCODING THE SAME

FIELD OF THE INVENTION

The present invention relates to a recombinant Δ9 desaturase capable of converting stearic acid, a saturated fatty acid, that is linked to glycerolipid, to oleic acid, an unsaturated fatty acid, and to an isolated gene encoding the same.

BACKGROUND OF THE INVENTION

The Δ9 desaturase of cyanobacterium is an enzyme converting stearic acid linking to glycerolipid to oleic acid, and converting palmitic acid linked to C-1 of glycerol to palmitoleic acid.

In the cyanobacterium, the desaturation process of fatty acids has been shown to be initiated through the induction of the double bond into a carbon chain at Δ9 position, followed by Δ12 and then Δ6 or Δ15. The Δ9 desaturase is an important enzyme which is responsible for the first step of a series of desaturation reactions, and is associated with the reaction of introducing the double bond into a carbon chain of stearic acid or palmitic acid at Δ9, which are linked to glycerolipid. This reaction requires reducing power, which depends on ferredoxin and NADPH.

On the other hand, an enzyme introducing the double bond into stearic acid at Δ9, which is not linked to glycerolipid, has been reported as stearoyl CoA desaturase in cytoplasm of animals and as stearoyl ACP (acyl-carrier protein) desaturase in chloroplast of plants. The DNA sequence of these enzymes has been determined.

The Δ9 desaturase of cyanobacteria is characterized by converting palmitic acid or stearic acid linking to glycerolipid to an unsaturated fatty acid, while the above two Δ9 desaturases can not catalyze this reaction. To appreciate the determinating factors of its substrate specificity, Δ9 desaturase of several species of cyanobacterium should be analyzed at the molecular level.

The phase transition temperature of biomembranes is dependant on the content of unsaturated fatty acids in the polar lipid membrane; therefore, the phase transition temperature falls as the content of an unsaturated fatty acids increases. It has been reported that the amount of unsaturated fatty acids in cyanobacterium increases due to the lower temperature, suggesting that the composition of fatty acids in cell membrane is also associated with the low-temperature tolerance of plants. Thus, the expression of fatty acid desaturase is considered to be adjusted by low temperature. Approaches to the elucidation of the mechanisms of adjustment of expression demand isolating the associated gene(s).

For these reasons, the isolation of the gene of Δ9 desaturase of cyanobacteria has been required, however, there has been no report of the isolation of this gene with an exception of the isolation from Anabaena variabilis.

DETAILED DESCRIPTION OF THE INVENTION

The present inventors have studied intensively for the purpose of analyzing the Δ9 desaturase of cyanobacteria at molecular level and isolated genomic DNA clone of Δ9 desaturase of cyanobacteria Synechocystis sp.PCC6803, using a genomic library of Synechocystis PCC6803, which led to the achievement of the present invention.

Therefore, the gist of the present invention lies in the Δ9 desaturase represented by the amino acid sequence shown in SEQ ID NO: 1 of the Sequence Listing, and an isolated gene encoding the same.

The present invention will be described in more detail below.

In the present invention, cyanobacteria (e.g., Synechocystis ps.PCC6803) is grown photoautotrophically, cells are disrupted with glass beads, and the genomic DNA is extracted by phenol extraction and ethanol precipitation.

The entire genomic DNA is digested partially with restriction enzyme (e.g., Sau3A) and ligated to phage vector (e.g., λDASH II) to produce genomic library. The genomic library is screened by plaque hybridization, wherein the coding region of Δ9 desaturase (which may be abbreviated to desC(A) hereinafter) of cyanobacteria Anabaena variabilis is used as a probe. Phage DNA is extracted from positive plaque. After digestion with a restriction enzyme(s), Southan hybridization is performed using the 0.75 Kb.p. DNA fragment of desC(A) as a probe. The DNA fragments which hybridized with probe DNA are sequenced by the dideoxy chain termination method.

The resultant base sequence of DNA fragments and amino acid sequence deduced therefrom are shown in SEQ ID NO: 1 of Sequence Listing.

The present invention also includes those derived from them through the deletion, replacement or addition of one or more amino acids or nucleotides from sequences shown in SEQ ID NO: 1 on condition that the Δ9 unsaturase activity of a polypeptide coded by the DNA fragments is not affected.

The homology of the resultant gene with desC(A) is then examined to identify it as a new member of the Δ9 desaturase gene family. The activity of Δ9 desaturase can be measured after expression of the new gene in E. coli. The activity of Δ9 desaturase can be assayed by extracting the membrane of E. coli transformed with the isolated gene, adding ferredoxin, NADPH and stearic acid thereto and measuring the formation of oleic acid.

Knoell and Knappe, Eur. J. Biochem. 50, 245–252 (1974) reported that ferredoxin, an electron donor, was found in E. coli. Therefore, the activity can be confirmed by ligating the isolated gene to an expression vector for E. coli., transforming E. coli. with the vector inducing the expression of Δ9 desaturase-encoding DNA, and detecting the production of oleic acid.

The resultant gene of Δ9 desaturase, for example, when it is introduced into plant cells, can be ligated to a promoter which expresses in plant cells (e.g., CaMV 35S etc.) and a terminator (e.g., NOS etc.) to produce a chimeric gene, which is then ligated to E. coli plasmid (e.g., pUC19, pBR322, etc.), amplified, and introduced into a plant cell using an electroporation method. The gene can be also transferred into plant cells by means of Agrobacterium by ligating it to Ti plasmid or Ri plasmid of Agrobacterium or by using them as a binary vector. The transformation of the gene can lead to the change in composition of fatty acid and the improvement of tolerance to low temperature.

The gene encoding Δ9 desaturase of cyanobacteria of the present invention is useful for improving the composition of fatty acids of animals, plants and microorganisms and for producing animals, plants or organisms which tolerate low temperature by transformation.

The present invention is further illustrated by the following examples, while the invention is not limited by these examples as far as it falls within the scope of the gist.

EXAMPLE (1) Extraction of Genomic DNA of Synechocystis PCC6803

A 300 ml of culture of Synechocystis PCC6803 (obtained from Pasteur Culture Collection) (the absorbance at 730 was between 5 and 10) was centrifuged at 4,500×g for 6 minutes, and 1–2 g of cells were collected. To 1 g of cells, 2 ml of sodium iodide solution (4 g sodium iodide/2 ml distilled water) was added and suspended by shaking. The suspension was incubated at 37° C. for 20 minutes and distilled water was added to a final volume of 40 ml, and the resulting solution was centrifuged at 10,000× g for 10 minutes. The pellet was added to 10 ml of DNA-extraction-buffer (50 mM Tris-HCl (pH 8.5), 50 mM Sodium Chloride and 5 mM EDTA) and 1.5 ml of lysozyme solution (50 mg/ml), and was incubated at 37° C. for 45 minutes. To the mixture was added 1 ml of 10% (w/v) N-lauroylsarcosine, and was incubated for another 20 minutes, while pipetting the disrupted cell solution several times in order to decrease the viscosity of the solution. To the disrupted cell solution was added 3 ml of ethidium bromide solution (10 mg/ml), and distilled water was added thereto to a final weight of 23 g. To the solution was added 21 g of cesium chloride and the mixture was centrifuged at 45,000× g for 20 hours. After removing ethidium bromide from the solution containing recovered chromosome DNA by mixing with 1-butanol repeatedly, the chromosome DNA solution was dialyzed against 4 liters of sterilized water for 90 minutes. After dialysis, the resulting DNA was extracted by an equal volume of phenol and then by an equal volume of chloroform, and was precipitated by ethanol. The precipitated DNA was collected by centrifugation and washed with 70% ethanol, dried, and dissolved in 100 μl of the buffer solution (10 mM Tris-HCl (pH 7.5)/0.1 mM EDTA).

(2) Screening of Genomic Library of Synechocystis PCC6803

The genomic DNA of Synechocystis PCC6803 was partially digested with the restriction endonuclease Sau3A, and was ligated into the BamHI site of phage vector-λDASH II. After infection of the phage containing genomic DNA of Synechocystis PCC6803 with E. coil, plaque hybridization was performed for 2,500 plaques using a 0.75 kb DNA fragment of the coding region of desC gene of Anabaena variabilis as a probe. Twenty two clones were selected from the plaques which hybridized to the probe and the phage DNA was extracted. Entire genomic DNA of Synechocystis PCC6803 was digested with HindIII and analyzed by Southern hybridization using the same probe as described above, resulting in the detection of 6.0 kb band. Among the positive clones, the one which contained a 6.0 Kb HindIII fragment was selected and the 6.0 kb HindIII fragment was subcloned into the HindIII site of plasmid Bluescript II Ks(+).

(3) Isolation of Δ9 Desaturase Gene (desC) of Synechocystis PCC6803

The plasmid DNA containing the HindIII fragment was extracted for the preparation of a physical map using restriction endnucleases, PstI, BamHI, EcoRI, SpeI and ApaI. Moreover, the plasmid DNA was digested with the above restriction endnucleases and Southern hybridization was performed using the DNA fragment containing desC gene used in plaque hybridization as a probe for limiting a homologous region.

The limited region was sequenced by the dideoxy chain termination method to discover a protein coding region (abbreviated to "ORF" hereinafter) consisting of 975 bases. This gene showed 64% homology at an amino acid level with desC(A) of Anabaena variabilis. Comparisons of Δ12 desaturase gene among cyanobacterium, in which Synechocystis PCC6803 (Wada et al., Nature, 347, 200–203 (1990)) have 59% homolgy to Anabaena variabilis (Sakamoto et al., Plant. Mol. Biol. 24, 643–650 (1994)) and 57% homology to Synechococcus PCC7002 (Sakamoto et al., Plant. Mol. Biol. 24, 643–650 (1994)), reveal a high homology between the isolated ORF and desC(A) of Anabaena variabilis. The ORF shares 31% and 30% homology with stearoyl CoA desaturase of rat and yeast, respectively (rat: Thiede et al., J. Biol. Chem. 261, 13230–13235 (1986); yeast: Stukey et al., J. Biol. Chem., 265, 20144–20149). These results led to the conclusion that the isolated ORF is Δ9 desaturase gene of Synechocystis PCC6803 (desC). The base sequence of the Synechocystis PCC6803 desC and the amino acid sequence deduced therefrom are presented in SEQ ID NO: 1 of Sequence Listing.

(4) Construction of Expression Vector and Expression of Δ9 Desaturase in E. coli The 0.5 kb fragment containing 5'-half region of des C obtained above was amplified by PCR and ligated into plasmid Bluescript II (pBSII). This DNA fragment was subcloned into the plasmid pBsII/H6 containing the 3'-half of the desC coding gegion and the resultant plasmid pBSII/desC was obtained. The pBSII/desC was digested with SpeI and a 1.1 kb DNA fragment containing a coding region was ligated into the NheI site of vector pET3a, which is located downstream from T7 bacteriophage promoter, and the pET3a/desC was obtained.

The pET3a/desC and, for comparison, pET3a which does not contain desC gene were transformed into E. coli BL21 (DE3) pLysS. Each transformant was cultured in LB medium containing stearic acid up to 0.6 of OD600 and further cultured for 1 hour with or without 1 mM IPTG. Cells were harvested by centrifugation, washed with 1.2% NaCl solution and collected again by centrifugation.

(5) Analysis of Fatty-Acid Composition of Individual Lipid Class of E. coli

Lipid was extracted from the collected E. coil by the method of Bligh and Dyer (Can. J. Biochem. Physiol., 37, 911–917 (1959)). The extracted lipid was separated into individual lipid class of PE (phosphatidyl ethanolamine), PG (phosphatidyl glycerol) and CL (cardiolipin) by silica gel thin-layer chromatography developed in $CHCl_3/CH_3OH/CH_3COOH$ (65:25:10). After separation, silica gel containing individual lipid class was scraped with a knife, and subjected to methanolysis in 5% HCl/methanol at 85° C. for 5.5 hours. The resultant methyl esters were extracted with 2 ml of n-hexane, concentrated and isolated by gas chromatography, and the content of individual lipid class was determined (Table 1).

The concentration of stearic acid in all lipid from E. coli grown in the medium without stearic acid was less than 1%, while in the medium with stearic acid the concentration was about 10%. As a control study, in E. coli transformed with pET3a, before and after the induction by IPTG, oleic acid did not increase and was less than 2% in any individual lipid class (Table 1). On the other hand, in E. coli transformed with pET3a/desC, the amount of oleic acid increased as a result of IPTG induction up to two or three times (from 2–5% to 6–10%) compared to that seen before induction (see Table 1, column 18:1(9)). The amount of palmitic acid, palmitoleic acid 16:1(a) and vaccenic acid 18:1(11) did not change.

TABLE 1

Changes in fatty-acid composition of individual lipid classes by introduction of the desC genes into E. coli.

| Lipid class | | 14:0 | 16:0 | 16:1(9) | 18:0 | 18:1(9) | 18:1(11) |
|---|---|---|---|---|---|---|---|
| | | | | (mol %) Before induction | | | |
| pET3a | | | | | | | |
| PE | (78%) | 2 | 31 ± 2 | 25 ± 1 | 14 ± 2 | t | 25 ± 1 |
| PG | (21%) | 1 | 27 ± 2 | 17 ± 1 | 16 ± 1 | 1 | 36 ± 1 |
| CL | ( 1%) | 1 | 32 ± 1 | 14 ± 1 | 19 ± 2 | 2 | 32 ± 2 |
| pET3a/desC | | | | | | | |
| PE | (80%) | 3 ± 1 | 34 ± 1 | 24 ± 1 | 10 ± 1 | 2 | 26 ± 1 |
| PG | (19%) | 1 | 31 ± 1 | 17 ± 1 | 10 ± 1 | 3 ± 1 | 36 ± 1 |
| CL | ( 1%) | 0 | 30 ± 1 | 11 ± 1 | 10 ± 2 | 5 ± 1 | 39 ± 1 |
| | | | | Induced by IPTG for 1 hr | | | |
| pET3a | | | | | | | |
| PE | (82%) | 4 ± 1 | 36 ± 3 | 24 ± 1 | 11 ± 2 | t | 23 ± 3 |
| PG | (17%) | 1 | 30 ± 2 | 15 ± 1 | 14 ± 1 | 1 | 39 ± 1 |
| CL | ( 1%) | 1 | 36 ± 1 | 12 ± 1 | 16 ± 2 | 1 | 33 ± 2 |
| pET3a/desC | | | | | | | |
| PE | (74%) | 3 ± 1 | 33 ± 1 | 24 ± 1 | 9 ± 1 | 6 ± 1 | 24 ± 1 |
| PG | (21%) | 1 | 30 ± 1 | 19 ± 1 | 8 ± 1 | 10 ± 1 | 31 ± 1 |
| CL | ( 5%) | 1 | 27 ± 1 | 18 ± 1 | 8 ± 1 | 10 ± 1 | 36 ± 1 |

Values were obtained from three independent cultures.
t: Trace (less than 0.5%).

(6) Analysis of Fatty Acid Composition at Each Bind Site of the Glycerol Skelton By the method as described above, fatty acids were extracted from E. coli induced by IPTG, and PE and PG were separated by silica gel thin-layer chromatography. These were selectively hydrolysed by the method of Fischer et al. (Hoppe-Seyler's Z. Physiol. Chem. 354, 1151–1123 (1973)) using lipase from Rhizopus delemar. After methanolysis, the amount of fatty acid methylester(s) was determined by gas chromatography.

In a control experiment where E. coli was transformed with pET3a, the rate of oleic acid in fatty acids linked to the C-1 position of glycerol skelton was less than 0.5% in either cases of PE and PG. On the other hand, in E. coli transformed with pET3a/desC, the rate of oleic acid in fatty acids linked to the C-1 position of glycerol skelton increased to 11% and 18% in the cases of PE and PG, respectively (Table 2). However, there is no difference in the C-2 position. The rate of palmitic acid, palmitoleic acid and vaccenic acid did not change.

These results indicate that the isolated gene encodes Δ9 desaturase which converts stearic acid linked to C-1 position of phospholipids to an unsaturated acid, regardless of polar residue.

TABLE 2

Positional distribution of fatty acids in individual lipid classes of E. coli cells transformed with the desC genes

| Lipid class (position) | | 14:0 | 16:0 | 16:1(9) | 18:0 | 18:1(9) | 18:1(11) |
|---|---|---|---|---|---|---|---|
| | | | | (mol %) | | | |
| pET3a | | | | | | | |
| PE | (C-1) | 1 | 68 | 6 | 16 | t | 5 |
| | (C-2) | 3 | 4 | 42 | 6 | 1 | 41 |
| PG | (C-1) | 1 | 51 | 12 | 16 | t | 20 |
| | (C-2) | 1 | 8 | 18 | 11 | 3 | 58 |
| pET3a/desC | | | | | | | |
| PE | (C-1) | 1 | 61 | 7 | 9 | 11 | 11 |
| | (C-2) | 3 | 5 | 41 | 9 | 1 | 37 |
| PG | (C-1) | 1 | 51 | 16 | 1 | 18 | 14 |
| | (C-2) | 1 | 7 | 22 | 18 | 2 | 48 |

Values were obtained from three independent cultures. The deviation of the values was within 2%.
t: Trace (less than 0.5%).

REFERENCE EXAMPLE

Isolation of Gene Encoding Anabaena Variabilis Δ9 Desaturase (1) Extraction of Genomic DNA A 300 ml of the culture of Anabaena variabilis strain M-3 (obtained from Institute of Applied Microbiology University of Tokyo) (absorbance at 730 was between 5 and 10) was centrifuged at 4,500× g for 8 minutes, and 1–2 g of cells were collected. To 1 g of cells, 2 ml of sodium iodide solution (4 g sodium iodide/2 ml distilled water) was added and suspended by shaking. The suspension was incubated at 37° C. for 20 minutes and distilled water was added to a final volume of 40 ml, and the resulting solution was centrifuged at 10,000 × g for 10 minutes. The pellet was resuspended in 10 ml of DNA-extraction-buffer (50 mM Tris-HCl (pH 8.5), 50 mM Sodium Chloride and 5 mM EDTA) and 5 ml of lysozyme solution (50 mg/ml), and was incubated at 37° C. for 45 minutes. To the mixture was added 1 ml of 10% (w/v) N-lauroylsarcosine, and it was incubated again for another 20 minutes, while pipetting the disrupted cell solution several times in order to decrease the viscosity of the solution. To the disrupted cell solution was added 3 ml of ethidium bromide solution (10 mg/ml), and distilled water was added thereto to a final weight of 23 g. To the solution was added 21 g of cesium chloride and the mixture was centrifuged at 45,000× g for 20 hours. After removing ethidium bromide from the solution containing recovered chromosome DNA by mixing with 1-butanol repeatedly, the chromosome DNA solution was dialyzed against 4 litters of sterilized water for 90 minutes. After dialysis, the resulting DNA was extracted by an equal volume of phenol and then by an equal volume of chloroform, and was precipitated by ethanol. The recipitated DNA was collected by centrifugation and washed by 70% ethanol, dried, and dissolved in 100 µl of the buffer (10 mM Tris-HCl (pH 7.5)/0.1 mM EDTA).

(2) The Isolation of the Δ12 Desaturase gene (desA) of *Anabaena Variabilis*

*Anabaena variabilis* DNA obtained as described above was partially digested with a restriction endonuclease Sau3A, and was ligated into the BamHI site of phage vector-λDASH II. After infection of the λphage including gemonic DNA of *Anabaena variabilis* with *E. coli*, plaque hybridization was performed for $3.5 \times 10^3$ plaques using 1.1 kb HincII-SpeI DNA fragment containing Δ12 desaturase gene (desA) of Synechocystis PCC6803 as a probe. Three clones were selected randomly from the plaques which hybridized to the probe. The phage DNA was extracted, digested with restriction endonuclease HincII and analyzed by Southern hybridization using the same probe as described above. In both phage DNA, 2.1 kb of bands hybridizing to the probe were found and one of them was examined for further identification of the gene.

The identification of the gene was performed as follows: Phage DNA was digested with restriction endonuclease EcoRI and Southern hybridization was performed to prove that a 7 kb fragment was homologous to the probe. This 7 kb fragment was ligated into the EcoRI site of shuttle vector pUC303 (Kuhlemier et al., Plasmid 10, 156–163 (1983)) between *E. coli* and Synechococcus PCC7942 to obtain pUC303/7-kb.

Since Synechococcus PCC7942 has fatty acids of 16:0, 16:1, 18:0 and 18:1, but does not have 16:2 and 18:2, this strain is considered to lack a Δ12 desaturase gene. It has been reported that introduction of desA gene of Synechococcus PCC6803 to Synechococcus PCC7942 led to production of unsaturated fatty acid of 16:2 and 18:2 (Wada et al., 1990 ibid). Synechococcus PCC7942 was then transformed with pUC303/7-kb by the method of Williams & Szalay, Gene, 24, 37–51 (1983). PCC7942 was cultured in 50 ml of BG-11 liquid medium up to $5-8 \times 10^7$/ml and centrifuged at 4,500× g for 10 minutes at room temperature. The precipitated cells were washed again with BG-11 medium, collected by centrifugation and suspended in BG-11 medium to a final concentration of $1-2 \times 10^9$ cells/ml. To 0.1 ml of the cell suspension was added 0.1 µg of DNA and shaked gently in the light for 1 hour. The transformed cells were grown in BG-11 agar medium containing 10 µg/ml of streptomycin, at the density of $1-5 \times 10^7$ cells/plate in the dark at 30° C. for 16 hours and further grown in the light for 8 hours. After 0.5 ml of 1 mg/ml of streptomycin was added dropwise to the agar medium, streptomycin resistant transformant cells producing green signal were chosen.

The transformant was grown in 100 ml of BG-11 medium, centrifuged at 4,500× g for 10 minutes and lyophilized. The dried cells were added to 10 ml of methanol containing 5% HCl (w/w) and heated at 85° C. for 2.5 hours for methanolysis. The resulting fatty acid methylester was extracted with 3 ml of n-hexane three times. After removal of hexane by evaporation, the sample was dissolved again in 0.1 ml of hexane. An aliquot of the sample solution was taken and used for analysis of fatty acid methylester composition by gas chromatography.

Synechococcus PCC7942 wild strain does not have unsaturated fatty acid of 18:2, while the cell transformed with pUC303/7-kb produced 1% of 18:2 unsaturated fatty acid in total fatty acid, therefore it was concluded that the desA gene of *Anabaena variabilis* was present in 7-kb EcoRI fragment.

Physical map was designed by digesting 7-kb EcoRI fragment with restriction endonuclease ClaI, SpeI and HindIII. Moreover, a region homologous to desA of synechocystis PCC6803 was identified by Southern hybridization and sequenced by the dideoxy chain termination method. Since an Open reading frame (ORF) composed of 1053 bases was found and three regions highly homologous to desA of Synechocystis PCC6803 (more than 80%) were noted in the amino acid sequence of ORF, it was concluded that this ORF was desA gene of *Anabaena variabilis*.

(3) Isolation of Δ9 Desaturase Gene (desC(A)) of *Anabaena Variabilis*

Determination of base sequence of 5' upstream *Anabaena variabilis* desA gene revealed an open reading frame (ORF) which was composed of 819 bases within about 1.2 kb. Since the amino acid sequence of this ORF product had 31% and 29% homology with stearoyl CoA desaturase of rat and yeast respectively, it was concluded that the ORF was Δ9 desaturase gene (desC(A)) of *Anabaena variabilis*. The base sequence of Anabaena variabilis desC(A) and the amino acid sequence deduced therefrom are presented in SEQ ID NO: 2 of Sequence Listing.

We claim:

1. An isolated gene encoding a recombinant Δ9 desaturase having the amino acid sequence shown in SEQ ID No. 3.

2. The gene according to claim 1, having the nucleic acid sequence shown in SEQ ID No. 1.

3. A recombinant vector which expresses the recombinant Δ9 desaturase encoded by the gene according to claim 1 or claim 2.

4. A transformant host cell comprising the recombinant vector according to claim 3.

5. A method for producing a recombinant Δ9 desaturase having the amino acid sequence shown in SEQ ID No. 3, which comprises growing the transformant according to claim 4 in a suitable medium and recovering the expression product.

* * * * *

SEQUENCE LISTING ( 1 ) GENERAL INFORMATION:

( i i i ) NUMBER OF SEQUENCES: 3

( 2 ) INFORMATION FOR SEQ ID NO:1:

(i) SEQUENCE CHARACTERISTICS:
   (A) LENGTH: 957 base pairs
   (B) TYPE: nucleic acid
   (C) STRANDEDNESS: double
   (D) TOPOLOGY: linear (ii) MOLECULE TYPE: Genomic DNA (vi) ORIGINAL SOURCE:
   (A) ORGANISM: Synechocystis PCC6803

(ix) FEATURE:
   (A) NAME/KEY: CDS
   (B) LOCATION: 1..954
   (C) IDENTIFICATION METHOD: S (xi) SEQUENCE DESCRIPTION: SEQ ID NO:1:

```
ATG TTA AAC CCA TTA AAC ATT GAA TAC CTA TAT TTA AGC AAA CTT TTT    48
Met Leu Asn Pro Leu Asn Ile Glu Tyr Leu Tyr Leu Ser Lys Leu Phe
 1               5                  10                  15

GAC AAT AGT TTA ATC GTT TTT AAC AAG CGC CAA TTA TTC CGT TTT TTC    96
Asp Asn Ser Leu Ile Val Phe Asn Lys Arg Gln Leu Phe Arg Phe Phe
                20                  25                  30

GTT AGG TTT TTT TTC ATG ACT GCT GCT CTT CCC AAC GAT TCC AAG CCC   144
Val Arg Phe Phe Phe Met Thr Ala Ala Leu Pro Asn Asp Ser Lys Pro
            35                  40                  45

AAG TTG ACT CCA GCT TGG ACT GTG ATC TTC TTT TTT ACC TCC ATT CAT   192
Lys Leu Thr Pro Ala Trp Thr Val Ile Phe Phe Phe Thr Ser Ile His
        50                  55                  60

TTG GTG GCC CTG TTG GCT TTC CTG CCC CAG TTT TTC AGT TGG AAA GCA   240
Leu Val Ala Leu Leu Ala Phe Leu Pro Gln Phe Phe Ser Trp Lys Ala
 65                 70                  75                  80

GTG GGG ATG GCT TTC TTG CTC TAT GTA ATT ACC GGC GGC ATT GGC ATT   288
Val Gly Met Ala Phe Leu Leu Tyr Val Ile Thr Gly Gly Ile Gly Ile
                85                  90                  95

ACT TTA GGT TTT CAC CGT TGT ATT TCC CAC CGC AGT TTC AAT GTT CCT   336
Thr Leu Gly Phe His Arg Cys Ile Ser His Arg Ser Phe Asn Val Pro
            100                 105                 110

AAA TGG TTA GAG TAT ATT TTC GTA ATC TGT GGC ACC CTA GCC TGT CAG   384
Lys Trp Leu Glu Tyr Ile Phe Val Ile Cys Gly Thr Leu Ala Cys Gln
        115                 120                 125

GGG GGC GTA TTT GAG TGG GTC GGC TTA CAC CGT ATG CAC CAC AAA TTT   432
Gly Gly Val Phe Glu Trp Val Gly Leu His Arg Met His His Lys Phe
130                 135                 140

TCT GAC ACC ACC CCG GAT CCC CAC GAT TCT AAT AAG GGT TTT TGG TGG   480
Ser Asp Thr Thr Pro Asp Pro His Asp Ser Asn Lys Gly Phe Trp Trp
145                 150                 155                 160

AGT CAC ATC GGC TGG ATG ATG TTT GAA ATT CCT GCT AAA GCT GAT ATT   528
Ser His Ile Gly Trp Met Met Phe Glu Ile Pro Ala Lys Ala Asp Ile
                165                 170                 175

CCC CGC TAC ACC AAG GAT ATC CAA GAC GAT AAA TTT TAT CAA TTT TGC   576
Pro Arg Tyr Thr Lys Asp Ile Gln Asp Asp Lys Phe Tyr Gln Phe Cys
            180                 185                 190

CAG AAT AAT CTA ATT CTT ATC CAG GTC GCC CTA GGC TTG ATT TTA TTT   624
Gln Asn Asn Leu Ile Leu Ile Gln Val Ala Leu Gly Leu Ile Leu Phe
        195                 200                 205

GCC TTA GGG GGC TGG CCC TTC GTT ATT TGG GGC ATT TTT GTC CGC CTA   672
Ala Leu Gly Gly Trp Pro Phe Val Ile Trp Gly Ile Phe Val Arg Leu
    210                 215                 220

GTG TTT GTT TTC CAC TTC ACT TGG TTT GTC AAC AGT GCC ACC CAT AAG   720
Val Phe Val Phe His Phe Thr Trp Phe Val Asn Ser Ala Thr His Lys
225                 230                 235                 240
```

| | | | | | | | | | | | | | | | | |
|---|---|---|---|---|---|---|---|---|---|---|---|---|---|---|---|---|
| TTC | GGC | TAC | GTT | AGC | CAT | GAA | TCC | AAT | GAT | TAT | TCC | CGC | AAT | TGT | TGG | 768 |
| Phe | Gly | Tyr | Val | Ser | His | Glu | Ser | Asn | Asp | Tyr | Ser | Arg | Asn | Cys | Trp | |
| | | | | 245 | | | | 250 | | | | | | 255 | | |
| TGG | GTA | GCA | TTG | TTA | ACT | TTC | GGT | GAA | GGT | TGG | CAC | AAT | AAT | CAC | CAC | 816 |
| Trp | Val | Ala | Leu | Leu | Thr | Phe | Gly | Glu | Gly | Trp | His | Asn | Asn | His | His | |
| | | | | 260 | | | | 265 | | | | | 270 | | | |
| GCC | TAT | CAG | TAC | TCT | GCT | CGC | CAT | GGT | TTG | CAA | TGG | TGG | GAA | GTG | GAT | 864 |
| Ala | Tyr | Gln | Tyr | Ser | Ala | Arg | His | Gly | Leu | Gln | Trp | Trp | Glu | Val | Asp | |
| | | 275 | | | | | 280 | | | | | 285 | | | | |
| TTA | ACT | TGG | ATG | ACC | ATT | AAA | TTC | CTA | TCT | TTG | CTG | GGG | TTA | GCC | AAG | 912 |
| Leu | Thr | Trp | Met | Thr | Ile | Lys | Phe | Leu | Ser | Leu | Leu | Gly | Leu | Ala | Lys | |
| | 290 | | | | | 295 | | | | | 300 | | | | | |
| GAT | ATT | AAA | CTT | CCT | CCG | GAA | ACT | GCG | ATG | GCC | AAC | AAA | GCC | TAG | | 957 |
| Asp | Ile | Lys | Leu | Pro | Pro | Glu | Thr | Ala | Met | Ala | Asn | Lys | Ala | | | |
| 305 | | | | | 310 | | | | | 315 | | | | | | |

(2) INFORMATION FOR SEQ ID NO:2:

(i) SEQUENCE CHARACTERISTICS:
        (A) LENGTH: 819 base pairs
        (B) TYPE: nucleic acid
        (C) STRANDEDNESS: double
        (D) TOPOLOGY: linear (ii) MOLECULE TYPE: Genomic DNA (vi) ORIGINAL SOURCE:
        (A) ORGANISM: Anabaena variabilis (ix) FEATURE:
        (A) NAME/KEY: CDS
        (B) LOCATION: 1..816
        (C) IDENTIFICATION METHOD: P (xi) SEQUENCE DESCRIPTION: SEQ ID NO:2:

| | | | | | | | | | | | | | | | | |
|---|---|---|---|---|---|---|---|---|---|---|---|---|---|---|---|---|
| ATG | ACA | ATT | GCT | ACT | TCA | ACT | AAA | CCT | CAA | ATC | AAC | TGG | GTA | AAT | ACC | 48 |
| Met | Thr | Ile | Ala | Thr | Ser | Thr | Lys | Pro | Gln | Ile | Asn | Trp | Val | Asn | Thr | |
| 1 | | | | 5 | | | | | 10 | | | | | 15 | | |
| CTA | TTT | TTC | CTT | GGG | CTA | CAC | ATC | GGC | GCT | TTG | TTT | GCC | TTT | ATC | CCT | 96 |
| Leu | Phe | Phe | Leu | Gly | Leu | His | Ile | Gly | Ala | Leu | Pha | Ala | Phe | Ile | Pro | |
| | | | 20 | | | | | 25 | | | | | 30 | | | |
| AGT | AAC | TTC | AGC | TGG | GCG | GCA | GTT | GGT | GTG | GCT | TTA | TTG | CTT | TAC | TGG | 144 |
| Ser | Asn | Phe | Ser | Trp | Ala | Ala | Val | Gly | Val | Ala | Leu | Leu | Leu | Tyr | Trp | |
| | | 35 | | | | | 40 | | | | | 45 | | | | |
| ATC | ACT | GGT | GGT | TTG | GGT | ATT | ACC | TTA | GGC | TTT | CAT | CGC | CTT | GTT | ACC | 192 |
| Ile | Thr | Gly | Gly | Leu | Gly | Ile | Thr | Leu | Gly | Phe | His | Arg | Leu | Val | Thr | |
| | 50 | | | | | 55 | | | | | 60 | | | | | |
| CAC | CGC | AGT | TTT | CAG | ACT | CCC | AAG | TGG | TTG | GAA | TAT | TTT | CTA | GTG | CTT | 240 |
| His | Arg | Ser | Phe | Gln | Thr | Pro | Lys | Trp | Leu | Glu | Tyr | Phe | Leu | Val | Leu | |
| 65 | | | | | 70 | | | | | 75 | | | | | 80 | |
| TGC | GGG | ACT | CTC | GCT | TGT | CAA | GGA | GGG | CCA | ATC | GAG | TGG | GTC | GGT | ACA | 288 |
| Cys | Gly | Thr | Leu | Ala | Cys | Gln | Gly | Gly | Pro | Ile | Glu | Trp | Val | Gly | Thr | |
| | | | | 85 | | | | | 90 | | | | | 95 | | |
| CAT | CGC | ATT | CAT | CAT | TTA | CAT | TCC | GAT | ACT | GAT | CCA | GAT | CCC | CAT | GAT | 336 |
| His | Arg | Ile | His | His | Leu | His | Ser | Asp | Thr | Asp | Pro | Asp | Pro | His | Asp | |
| | | | | 100 | | | | 105 | | | | | 110 | | | |
| TCT | AAT | AAA | GGT | TTC | TGG | TGG | AGC | CAT | ATT | GGT | TGG | CTA | ATT | TAT | CAC | 384 |
| Ser | Asn | Lys | Gly | Phe | Trp | Trp | Ser | His | Ile | Gly | Trp | Leu | Ile | Tyr | His | |
| | | 115 | | | | | 120 | | | | | 125 | | | | |
| TCT | CCC | TCC | CAC | GCT | GAT | GTT | CCT | CGG | TTC | ACC | AAA | GAT | ATT | GCC | GAA | 432 |
| Ser | Pro | Ser | His | Ala | Asp | Val | Pro | Arg | Phe | Thr | Lys | Asp | Ile | Ala | Glu | |
| | 130 | | | | | 135 | | | | | 140 | | | | | |
| GAC | CCA | GTC | TAT | CAG | TTT | TTA | CAG | AAA | TAT | TTC | ATT | TTT | ATC | CAG | ATT | 480 |
| Asp | Pro | Val | Tyr | Gln | Phe | Leu | Gln | Lys | Tyr | Phe | Ile | Phe | Ile | Gln | Ile | |
| 145 | | | | | 150 | | | | | 155 | | | | | 160 | |

```
GCT  CTG  GGG  TTG  TTG  CTG  TTA  TAT  CTA  GGC  GGG  TGG  TCT  TTT  GTG  GTC      528
Ala  Leu  Gly  Leu  Leu  Leu  Leu  Tyr  Leu  Gly  Gly  Trp  Ser  Phe  Val  Val
               165                      170                      175

TGG  GGA  GTT  TTC  TTT  CGC  ATC  GTT  TGG  GTT  TAC  CAC  TGT  ACT  TGG  TTG      576
Trp  Gly  Val  Phe  Phe  Arg  Ile  Val  Trp  Val  Tyr  His  Cys  Thr  Trp  Leu
               180                      185                      190

GTA  AAC  AGC  GCT  ACC  CAT  AAG  TTT  GGC  TAC  CGC  ACC  TAT  GAT  GCT  GGT      624
Val  Asn  Ser  Ala  Thr  His  Lys  Phe  Gly  Tyr  Arg  Thr  Tyr  Asp  Ala  Gly
               195                      200                      205

GAC  AGA  TCC  ACT  AAC  TGT  TGG  TGG  GTA  GCT  GTC  CTA  GTG  TTT  GGT  GAA      672
Asp  Arg  Ser  Thr  Asn  Cys  Trp  Trp  Val  Ala  Val  Leu  Val  Phe  Gly  Glu
               210                      215                      220

GGT  TGG  CAC  AAC  AAC  CAC  CAC  GCT  TTT  CAA  TAT  TCA  GCT  CGT  CAC  GGG      720
Gly  Trp  His  Asn  Asn  His  His  Ala  Phe  Gln  Tyr  Ser  Ala  Arg  His  Gly
225                 230                      235                      240

TTG  GAA  TGG  TGG  GAA  GTT  GAT  CTG  ACT  TGG  ATG  ACA  GTG  CAA  TTG  CTG      768
Leu  Glu  Trp  Trp  Glu  Val  Asp  Leu  Thr  Trp  Met  Thr  Val  Gln  Leu  Leu
                    245                      250                      255

CAA  ATA  CTC  GGT  TTA  GCA  ACT  AAT  GTC  AAA  CTA  GCA  GAC  AAA  AAG  CAG      816
Gln  Ile  Leu  Gly  Leu  Ala  Thr  Asn  Val  Lys  Leu  Ala  Asp  Lys  Lys  Gln
               260                      265                      270

TAA                                                                                  819
```

(2) INFORMATION FOR SEQ ID NO:3:

(i) SEQUENCE CHARACTERISTICS:
        (A) LENGTH: 318 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:3:

```
Met  Leu  Asn  Pro  Asn  Ile  Glu  Tyr  Leu  Tyr  Leu  Ser  Lys  Leu  Phe
 1                  5                       10                      15

Asp  Asn  Ser  Leu  Ile  Val  Phe  Asn  Lys  Arg  Gln  Leu  Phe  Arg  Phe  Phe
               20                      25                      30

Val  Arg  Phe  Phe  Phe  Met  Thr  Ala  Ala  Leu  Pro  Asn  Asp  Ser  Lys  Pro
               35                      40                      45

Lys  Leu  Thr  Pro  Ala  Trp  Thr  Val  Ile  Phe  Phe  Thr  Ser  Ile  His
     50                      55                      60

Leu  Val  Ala  Leu  Leu  Ala  Phe  Leu  Pro  Gln  Phe  Ser  Trp  Lys  Ala
65                       70                      75                      80

Val  Gly  Met  Ala  Phe  Leu  Leu  Tyr  Val  Ile  Thr  Gly  Gly  Ile  Gly  Ile
               85                      90                      95

Thr  Leu  Gly  Phe  His  Arg  Cys  Ile  Ser  His  Arg  Ser  Phe  Asn  Val  Pro
               100                     105                     110

Lys  Trp  Leu  Glu  Tyr  Ile  Phe  Val  Ile  Cys  Gly  Thr  Leu  Ala  Cys  Gln
               115                     120                     125

Gly  Gly  Val  Phe  Glu  Trp  Val  Gly  Leu  His  Arg  Met  His  His  Lys  Phe
     130                     135                     140

Ser  Asp  Thr  Thr  Pro  Asp  Pro  His  Asp  Ser  Asn  Lys  Gly  Phe  Trp  Trp
145                     150                     155                     160

Ser  His  Ile  Gly  Trp  Met  Met  Phe  Glu  Ile  Pro  Ala  Lys  Ala  Asp  Ile
               165                     170                     175

Pro  Arg  Tyr  Thr  Lys  Asp  Ile  Gln  Asp  Asp  Lys  Phe  Tyr  Gln  Phe  Cys
               180                     185                     190
```

-continued

| Gln | Asn | Asn 195 | Leu | Ile | Leu | Ile | Gln 200 | Val | Ala | Leu | Gly | Leu 205 | Ile | Leu | Phe |
| Ala | Leu 210 | Gly | Gly | Trp | Pro | Phe 215 | Val | Ile | Trp | Gly | Ile 220 | Phe | Val | Arg | Leu |
| Val 225 | Phe | Val | Phe | His | Phe 230 | Thr | Trp | Phe | Val | Asn 235 | Ser | Ala | Thr | His | Lys 240 |
| Phe | Gly | Tyr | Val | Ser 245 | His | Glu | Ser | Asn | Asp 250 | Tyr | Ser | Arg | Asn | Cys 255 | Trp |
| Trp | Val | Ala | Leu 260 | Leu | Thr | Phe | Gly | Glu 265 | Gly | Trp | His | Asn | Asn 270 | His | His |
| Ala | Tyr | Gln 275 | Tyr | Ser | Ala | Arg | His 280 | Gly | Leu | Gln | Trp | Trp 285 | Glu | Val | Asp |
| Leu | Thr 290 | Trp | Met | Thr | Ile | Lys 295 | Phe | Leu | Ser | Leu | Leu 300 | Gly | Leu | Ala | Lys |
| Asp 305 | Ile | Lys | Leu | Pro | Pro 310 | Glu | Thr | Ala | Met | Ala 315 | Asn | Lys | Ala | | |